United States Patent
Tanaka et al.

[11] Patent Number: 5,716,507
[45] Date of Patent: Feb. 10, 1998

[54] OXYGEN SENSOR ELEMENT

[75] Inventors: Akio Tanaka, Obu; Naoto Miwa, Tsushima; Tositaka Saito, Toyohashi; Hiromi Sano, Nagoya, all of Japan

[73] Assignee: Nippondenso Co., Ltd., Kariya, Japan

[21] Appl. No.: 571,229

[22] Filed: Dec. 12, 1995

[30] Foreign Application Priority Data

Dec. 13, 1994 [JP] Japan .................... 6-333049

[51] Int. Cl.$^6$ ................................ G01N 27/407
[52] U.S. Cl. ................ 204/424; 204/428; 204/429; 264/56; 427/125; 427/126.3; 427/404; 427/419.2
[58] Field of Search .................. 204/421–429; 205/783.5, 784, 784.5, 785

[56] References Cited

U.S. PATENT DOCUMENTS

| | | | |
|---|---|---|---|
| 3,843,400 | 10/1974 | Radford et al. | 204/421 |
| 4,021,326 | 5/1977 | Doller et al. | 204/429 |
| 4,225,634 | 9/1980 | Tanaka et al. | 204/429 |
| 4,257,863 | 3/1981 | Hoffman | 204/429 |
| 4,359,374 | 11/1982 | Sano et al. | |
| 4,402,820 | 9/1983 | Sano et al. | 204/429 |
| 4,477,487 | 10/1984 | Kojima et al. | |
| 4,863,583 | 9/1989 | Kurachi et al. | 204/424 |
| 5,520,789 | 5/1996 | Takahashi et al. | 204/424 |

FOREIGN PATENT DOCUMENTS

| | | |
|---|---|---|
| 53-029187 | 3/1978 | Japan . |
| 53-078885 | 7/1978 | Japan . |
| 55-36105 | 9/1980 | Japan . |
| 56-043507 | 10/1981 | Japan . |
| 62-45496 | 9/1987 | Japan . |

*Primary Examiner*—T. Tung
*Attorney, Agent, or Firm*—Cushman, Darby & Cushman IP Group of Pillsbury Madison & Sutro LLP

[57] ABSTRACT

An oxygen sensor element for detecting an oxygen concentration, the oxygen sensor includes a solid electrolyte; a porous film covering the solid electrolyte at the gas-measuring side; and a reaction electrode provided on the porous film; wherein the porous film includes ceramic particles and metallic particles, and the metallic particles are bonded with the reaction electrode by a metallic bond. In this way, the porous film includes the ceramic particles and the metallic particles to form an irregular surface, and the reaction electrode is adhered to the irregular surface of the porous film in such a manner that the electrode bites into the surface of the porous film. The metallic particles in the irregular surface of the porous film are tightly bonded to the reaction electrode by the metallic bond.

4 Claims, 4 Drawing Sheets

OXYGEN SENSOR ELEMENT

CROSS REFERENCE TO RELATED APPLICATION

This application is based on and claims priority from Japanese applications No. 6-333049 filed on Dec. 13, 1994, the content of which is incorporated herein by reference.

BACKGROUND OF THE INVENTION

1. Field of the Invention

The present invention relates to an oxygen sensor element for use in air fuel control of automobile engines or the like, and to a method for manufacturing the same.

2. Related Art

Conventionally, an oxygen sensor element comprising a solid electrolyte, a film at the gas measuring side of the solid electrolyte, and a reaction electrode on the film formed by means of chemical slating, evaporation, etc., has been proposed, as disclosed in Japanese Patent Publication No. Sho. 55-36105 or Japanese Patent Publication 62-45496. The film is formed by adhering and sintering zirconia particles or the like to the solid electrode.

The above mentioned coventional film prevents the reaction electrode from exfoliating and improves the durability of the oxygen sensor element. That is to say, the metallic reaction electrode cannot be directly joined with a ceramic solid electrolyte, however, the film is also made of zirconia ceramics in the same way as the solid electrolyte and can be adhered to the solid electrolyte as a unit.

The above film includes an irregular (concave and convex) surface, and therefore, the reaction electrode can be adhered to the film in such a manner that the reaction electrode bites into the irregular surface. The oxygen sensor configured described as above is superior in the durability, because the exfoliation of the reaction electrode is minimized.

However, in recent years, the oxygen sensor elements, particularly used in automobile engines, are more frequently used in a higher temperature in view of strengthening of exhaust gas regulations and the market tendency for further improved, fuel consumption. Accordingly, the oxygen sensor element is required to satisfy superior heat resistance.

The conventional oxygen sensor element described above cannot achieve sufficiently high heat resistance when used under high temperature. That is to say, in the oxygen sensor element, the reaction electrode of the oxygen sensor element is adhered simply by a mechanical effect where the reaction electrode bites into the irregular surface. The mechanical adhesion force is not strong enough to prevent the reaction electrode from aggregating at high temperature.

Accordingly, the sensor characteristics of the oxygen sensor elements is deteriorated in a short period of time when used at a higher temperature, because the reaction electrode aggregates and the electric conductivity between the solid electrolyte and the reaction electrode is lost.

SUMMARY OF THE INVENTION

In view of the above circumstances, the present invention provides an oxygen sensor which is superior in the heat resistance and durability and a method for manufacturing the same.

According to a first aspect of the present invention, an oxygen sensor element includes a solid electrolyte, a porous film covering said solid electrolyte at the gas-measuring side, and a reaction electrode provided on the porous film. The porous film includes ceramic particles and metallic particles, and the metallic particles are bonded with the reaction electrode by a metallic bond.

In the first aspect of the present invention, the metallic particles incorporated in the porous film are bonded with the reaction electrode by a metallic bond, and the metallic particles do not aggregate when heated.

The metallic particles may be already aggregated in advance by heating and sintering or the like at a high temperature in the manufacturing process. In such a case, the metallic particles have already aggregated at a high temperature by heating; therefore, such metallic particles will not re-aggregate at a temperature not higher than the previous temperature.

It is preferable that the metallic particles be made of the same substance as that used fox the reaction electrode. Otherwise, it is preferable that the metallic particles are made of a substance capable of being bonded with the reaction electrode by a metallic bond.

Examples of substances suitable for fabricating the metallic particles include substances having the same crystalline structure as substances having lattice constants similar to those of the substance composing the reaction electrode. More specifically, in case platinum is used for the reaction electrode, for instance, the metallic particles can be made of platinum, palladium, rhodium, iridium, etc. The crystalline structure of these substances can be characterized as face centered cubic lattice, which is the same as platinum. Furthermore, the lattice constants for the substances are in a range from 3.80 to 3.83 Å, which are in the vicinity of 3.92 Å, the lattice constant of platinum.

It is preferable that the ceramic particles be made of the same material as that used for the solid electrolyte. In this way, the adhesion strength between the porous film and the solid electrolyte can be increased, and the reactive electrode can be prevented from being exfoliated together with the porous film from the solid electrolyte.

It is preferable that the metallic particles contained in the porous film constitute from 1 to 50% by weight of the porous film. If the concentration of the metallic particles contained in the porous film is less than 1% by weight, the effect for preventing the aggregation in the reaction electrode is lowered, and it may not be possible to prevent the sensing characteristics from being deteriorated. On the other hand, if the concentration of the metallic particles contained in the porous film is more than 50% by weight, the porous film may be exfoliated from the solid electrolyte. The preferable upper limit of the concentration of the metallic particles is 10% by weight of the porous film.

A preferable porosity of the porous film is in a range from 5 to 30%. In a case where the porosity of the film is less than 5%, the effect for preventing aggregation in the reaction electrode is lowered, and it may not be possible to prevent the sensing characteristics from being deteriorated. If the porosity is more than 30%, the porous film may be exfoliated from the solid electrolyte. The preferable upper limit of the porosity is 10%.

It is preferable that an average diameter of metallic particles be in a range from 0.01 μm–1.0 μm. If the average diameter of the metallic particles is less than 0.01 μm, the metallic particles may aggregate easily at the sintering temperature of the solid electrolyte. If the average diameter of the metallic particles is more than 1.0 μm, the existence ratio of the metallic particles in the porous film is decreased and the number of the metallic particles is decreased.

Therefore, metallic bonding portions between the porous film and the reaction electrode are reduced, and the bonding strength between the solid electrolyte and the reaction electrode is deteriorated.

The oxygen sensor element according to the present invention can be applied to all types of oxygen sensors, such as an oxygen concentration electromotive force-type oxygen sensor, a limiting current-type oxygen sensor, etc.

According to a second aspect of the present invention, a method for manufacturing the oxygen sensor element includes steps of: forming a layer of a composite material comprising ceramic particles and metallic particles on the solid electrolyte; forming the porous film by sintering the composite material layer at a predetermined temperature under which the metallic particles aggregate; and forming the reaction electrode on the surface of the porous film.

It is preferable that the sintering temperature be higher than the temperature at which the oxygen sensor is used to measure an oxygen concentration. In this way, the metallic particles do not aggregate at a heating temperature not higher than the sintering temperature.

More specifically, it is preferable that the sintering temperature be in a range from 1,000° to 1,600° C. when the oxygen sensor element is used in the control of the air/fuel ratio of an automobile engine. If the sintering temperature is lower than 1,000° C., during the operation, the metallic particles aggregate in the reaction electrode. If the sintering temperature is more than 1,600° C., abnormal grain growth may be caused during combustion.

The sintering temperature differs depending on the type of the metallic particles. In case that platinum is used for the metallic particles, it is preferable that the sintering temperature be in a range from 1,200° to 1,600° C. If the sintering temperature is lower than 1,200° C., metallic particles may aggregate, and if the sintering temperature is more than 1,600° C., platinum may be volatilized during combustion.

It is preferable that the porous film be etched by a strong acid such as hydrofluoric acid after being sintered. In this way, a surface furnished with more deeply perforated irregularities can be obtained. Therefore, the mechanical adhesive force between the porous film and the reaction electrode can be increased.

According to a third aspect of the present invention, a method for manufacturing the oxygen sensor element includes steps of: forming a layer of a ceramic material comprising ceramic particles on the gas-measuring side of the solid electrolyte; forming a ceramic porous film by sintering the ceramic material layer; immersing the ceramic porous film in a solution of a metallic salt to form metallic particles by decomposing the metallic salt; aggregating the metallic particles by heating; and forming the reaction electrode on the surface of the porous film.

The ceramic porous film can be formed by permeating a metallic salt into a ceramic material layer by, for example, immersing the ceramic material layer into a solution of the metallic salt, and drying the ceramic material thereafter. Usable metallic salts for a platinum reaction electrode include chlorides, nitrates, cyanides, etc., of platinum, palladium, rhodium, iridium, etc.

After permeating the ceramic material with the metallic salt, the salt can be decomposed by, for instance, heating, reduction, or ion exchange. The most preferable method for decomposition is by heating. The decomposition and aggregation can be performed continuously in a single heating treatment.

Furthermore, it is preferable that the porous film be etched after being sintered. It is also preferable that the concentration of the metallic particles contained in the porous film be 1 to 50% by weight of metallic particles.

According to the present invention, the porous film includes the ceramic particles and the metallic particles to form an irregular surface, and the reaction electrode is adhered to the irregular surface of the porous film in such a manner that the electrode bites into the surface of the porous film. The metallic particles in the irregular surface of the porous film are tightly bonded to the reaction electrode by metallic bond. Thus, the porous film and the reaction electrode are bonded extremely tightly with each other.

The metallic particles in the porous film are thermally stable, and would not aggregate by heating during the operation of the sensor element. Thus, the oxygen sensor element comprises a reaction electrode tightly bonded and fixed to the porous film without aggregating by heating. In short, the oxygen sensor element according to the present is superior in heat resistance and durability.

Furthermore, the solid electrolyte is made of the ceramic body, and the porous film contains ceramic particles, and therefore, both are tightly bonded to each other.

Thus, according to the method for manufacturing an oxygen sensor element of the present invention, an oxygen sensor element which is superior in the heat resistance and durability can be obtained.

BRIEF DESCRIPTION OF THE DRAWINGS

Additional objects and advantages of the present invention will be more readily apparent from the following detailed description of preferred embodiments thereof when taken along together with accompanying drawings in which.

DETAILED DESCRIPTION OF THE PREFERRED EMBODIMENTS

The present invention is described in further detail below referring to the preferred embodiments according to the present invention. It should be understood, however, that the present invention is not to be construed as being limited to the examples below.

Figure 1:
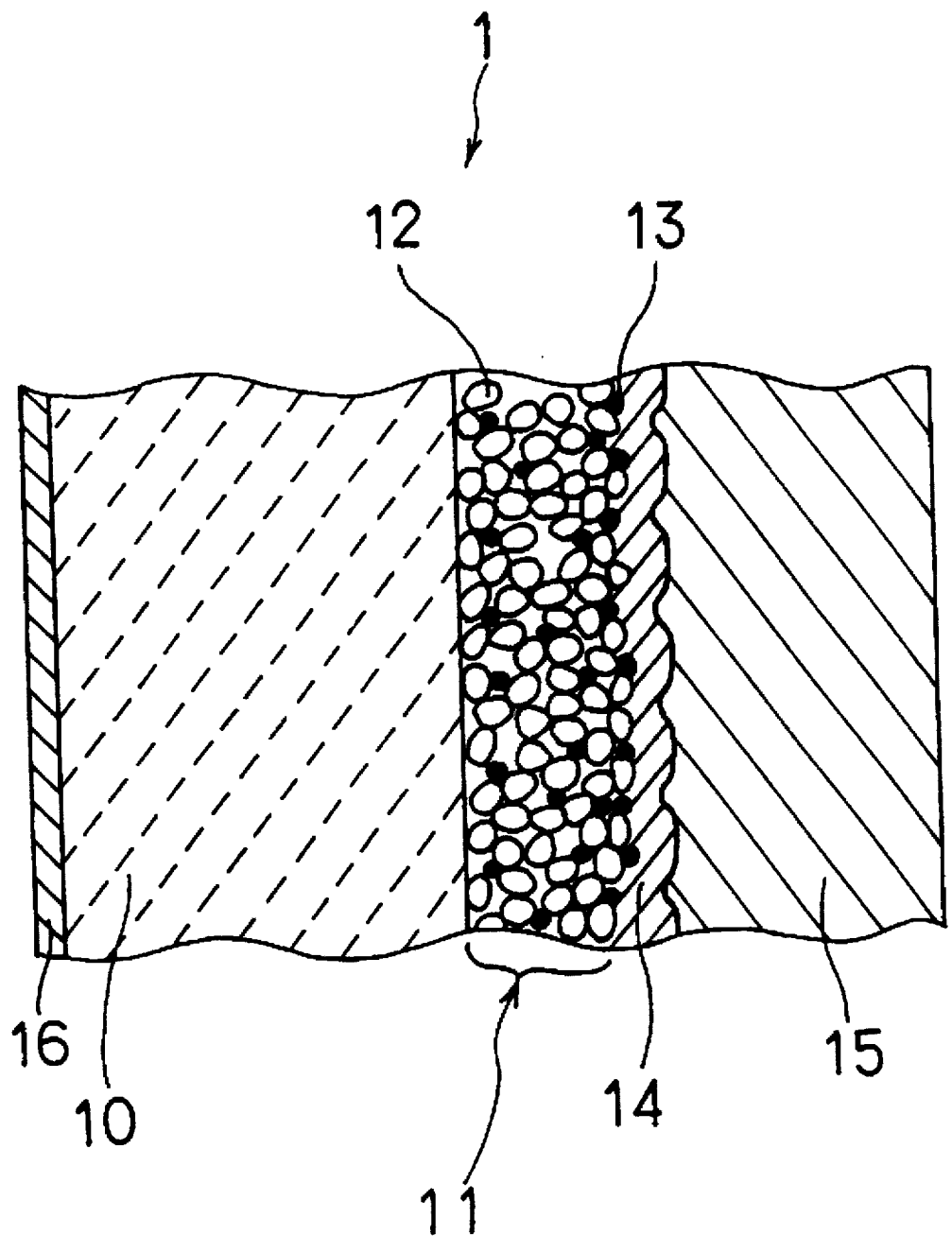
FIG. 1 is a cross sectional view of a main portion of an oxygen sensor element of a first embodiment according to the present invention.
Figure 2:
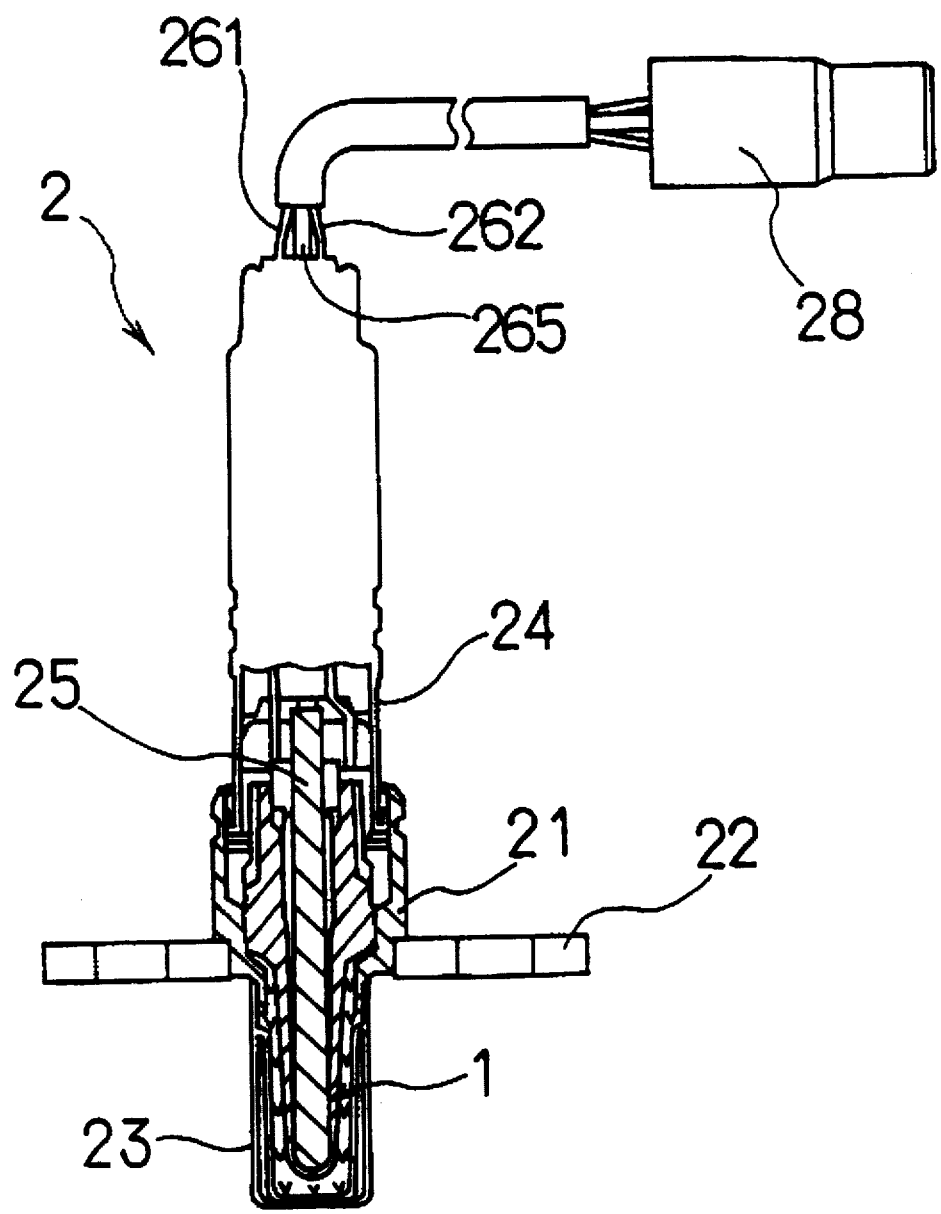
FIG. 2 is an explanatory view for the oxygen sensor element of the first embodiment according to the present invention.
Figure 3:
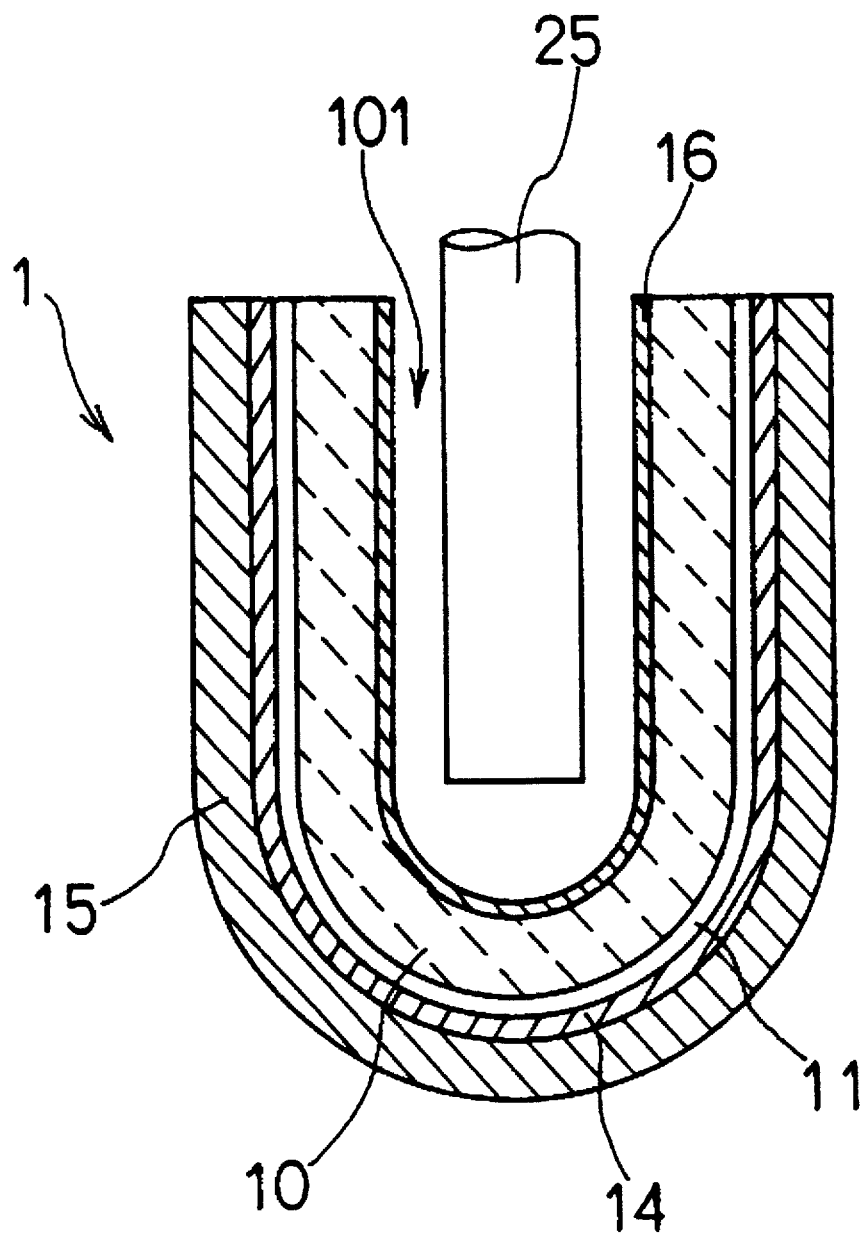
FIG. 3 is a cross sectional explanatory view of the oxygen sensor element of the first embodiment according to the present invention.

Referring to FIGS. 1 to 3, an oxygen sensor element according to a first embodiment of the present invention and an oxygen sensor equipped with the element are described below. The oxygen sensor of this embodiment is an oxygen concentration electromotive force-type oxygen sensor.

As shown in FIG. 1, the oxygen sensor element 1 comprises a solid electrolyte 10 having a platinum reaction electrode 14 provided on the surface of the gas-measuring side of the electrolyte so as to hold a porous film 11 therebetween. The porous film 11 comprises heat-resistant ceramic particles 12 and heat-resistant metallic particles 13, and the metallic particles 13 are bonded with the reaction electrode 14 by a metallic bonding. The metallic particles 13 are not aggregated by heating when the oxygen sensor element 1 measures an oxygen concentration.

A $ZrO_2$ ceramic body constitutes the solid electrolyte 10. The heat-resistant ceramic particles 12 in the porous film 11 are $ZrO_2$ particles having a diameter of about 1 μm, and the heat-resistant particles 13 are platinum particles having a maximum diameter of about 1 μm. The metallic particles 13 are contained in the porous film 11 in a concentration of 10% by weight of the porous film 11. The porosity of the porous film 11 is 10%.

The metallic particles 13 are heated in advance at a temperature not lower than the temperature at which the metallic particles 13 begin to aggregate (more specifically, a temperature in a range from 1,400° to 1,600° C.), which will be described later.

The surface of the reaction electrode 14 is covered with a coating layer 15 comprising $MgO.Al_2O_3$ spinel. A platinum inner electrode 16 is provided on the surface of the solid electrolyte 10 at the side of the standard gas.

Next, an oxygen sensor 2 equipped with the oxygen sensor element 1 of this embodiment is described.

As shown in FIG. 2, the oxygen sensor 2 of this embodiment comprises an oxygen sensor element 1, a housing 21 for fixing the oxygen sensor element 1, an exhaust side cover 23 provided on the lower side of the housing 21 to surround the oxygen sensor element 1, and an atmosphere side cover 24 provided on the upper side of the housing 21.

The reaction electrode 14 and the inner electrode 16 of the oxygen sensor element 1 are connected to an upper connector 28 located at the upper side of the oxygen sensor via leads 261 and 262. As shown in FIGS. 2 and 3, the solid electrolyte 10 of the oxygen sensor element 1 is in the form of a cylinder with a bottom end, and a heater 25 is inserted into the inner cavity 101 of the solid electrolyte 10. The heater 25 is connected to the upper connector 28 via a lead 265.

In FIG. 2, a flange 22 is used for mounting the oxygen sensor to an exhaust pipe (not shown) or the like.

An operation of the embodiment is described. The porous film 11 in the oxygen sensor element 1 of this embodiment has an irregular surface, and the reaction electrode 14 can be adhered to the porous film so as to bite into the irregular surface.

The metallic particles 13 in the irregular surface of the porous film 11 are bonded to the reaction electrode 14 by a metallic bond. Thus, an extremely strong bonding between the porous film 11 and the reaction electrode 14 is obtained.

The metallic particles 13 in the porous film 11 are thermally stable, and would not aggregate by being heated during operation. Accordingly, the reaction electrode 14 is strongly attached and fixed to the porous film 11 at a high temperature, thereby preventing the aggregation in the reaction electrode 14.

In short, the oxygen sensor element 1 of this embodiment is superior in heat resistance and durability.

Furthermore, since the solid electrolyte 10 of the oxygen sensor element 1 is made of a ceramic body while the porous film 11 contains ceramic particles 12, strong bonding between the solid electrolyte 10 and the porous film 11 can be obtained.

According to the embodiment described above, the oxygen sensor element which is superior in the excellent heat resistance and durability can be provided.

The oxygen sensor element of this embodiment can be applied to a limited current type oxygen sensor.

Next, a method for manufacturing the oxygen sensor element of the first embodiment is described.

Ceramic powder containing $ZrO_2$ is pressure molded into a cylinder having a bottom end. The molded product is sintered at 1,200° C. to obtain a solid electrolyte.

Then, a composite material composed of heat-resistant ceramic particles and metallic particles is prepared. The ceramic particles consist of $ZrO_2$ particles each having a diameter of about 1 μm. The metallic particles consist of platinum, and have a maximum diameter of about 1 μm.

A water-soluble slurry comprising an organic binder is added to the mixture of the ceramic particles and the metallic particles, and the mixture is kneaded to obtain the composite material. Next, the composite material is applied to the surface of the solid electrolyte to provide a composite material layer. Then, the composite material layer is sintered together with the solid electrolyte at a temperature in a range from 1,400° to 1,600° C. to obtain a porous film.

The surface of the porous film is etched for several minutes by using hydrofluoric acid. A reaction electrode consisting of platinum is provided to the surface of the porous film by chemical plating. A coating layer consisting of a $MgO.Al_2O_3$ spinel is formed by plasma spraying.

An inner electrode is provided on the inner side, i.e., the standard gas side, of the solid electrolyte in the same manner as the reaction electrode described above.

Thus, the oxygen sensor element can be obtained.

In the method for manufacturing the oxygen sensor element according to the embodiment, the composite material layer is sintered at a high temperature in the range from 1,400° to 1,600° C. By sintering at the high temperature, the metallic particles aggregate and are thermally stabilized. The oxygen sensor element is used for detecting the oxygen concentration of a gas exhausted from an engine. Therefore, the practical operation is at a temperature not higher than the maximum temperature of the exhaust gas, i.e., about 900° C. Accordingly, the metallic particles will not re-aggregate when heated by the exhaust gas to a temperature not higher than the sintering temperature.

The method for manufacturing the oxygen sensor element which is superior in heat resistance and durability can be obtained.

Figure 4:
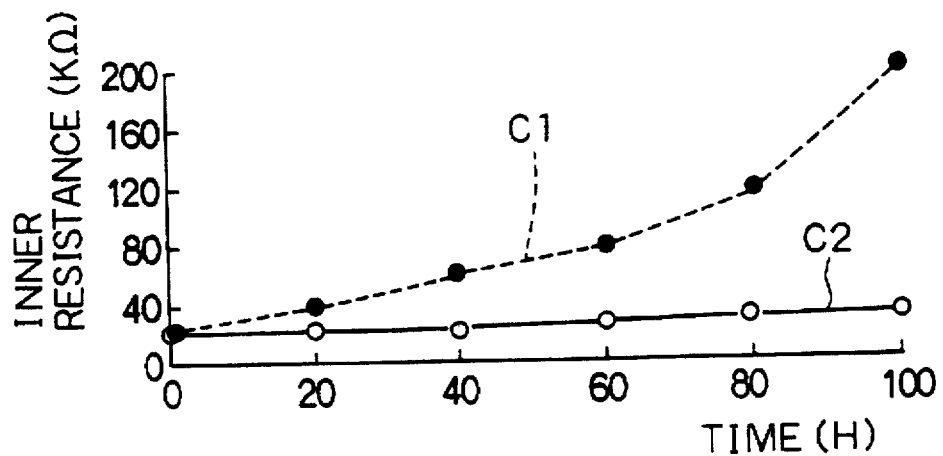
FIG. 4 is a graph showing the relationship between the inner resistance of the oxygen sensor element and the time passage in the heat resistance test of the first embodiment.

Next, the heat resistance of the oxygen sensor element of the embodiment in comparison with a comparative example is described referring to FIG. 4.

Sample No. 2 is an oxygen sensor element having the same structure shown in FIGS. 1 to 3, and the details are given in Table 1. Sample No. C1 is provided as a comparative example, and the details are also shown in Table 1.

The heat resistance is evaluated by putting samples No. 2 and No. C1 in an electric furnace and by heating them in an atmosphere of air to a temperature of 1,000° C.

If the reaction electrode of an oxygen sensor element aggregates or exfoliate, the inner resistance of the oxygen sensor element rises in accordance with the decrease in the electric conductivity of the reaction electrode. Thus, the heat resistance of samples No. 2 and No. C1 can be evaluated by measuring the inner resistance of the oxygen sensor elements of the samples.

FIG. 4 shows the measured results. In FIG. 4, the abscissa represents the time passage from the start of the test, and the ordinate represents the inner resistance of the samples No. 2 and No. C1.

As seen from FIG. 4, the inner resistance of the sample No. 2 is the same as that of sample No. C1 at the beginning of the test, but the difference between the inner resistances of the sample No. 2 and the sample No. C1 increases as the time passes.

The inner resistance of the sample No. 2 remains almost unchanged even after 100 hours has passed. In contrast to the sample No. 2, the inner resistance of the sample C1 quickly increases as the time passes.

It is understood that the sample No. 2 is an oxygen sensor element which is superior in heat resistance and durability so that the initial characteristics can be maintained even when the oxygen sensor is heated at a high temperature for a long time.

The heat resistance of the oxygen sensor element and the adhesion strength of the porous film in comparison with a comparative example is described with reference to Table 1.

As shown in Table 1, each of the samples No. 1 to No. 6 has the same structure as the oxygen sensor element shown in FIGS. 1 to 3, however, these samples differs in the kind of the metallic particles, the amount of the content of the metallic particles, or porosity, etc.

Sample No. C1 as a comparative example contains no metallic particles in the porous film. Each of samples No. C2 to No. C4 as comparative examples has the same structure as the oxygen sensor element shown in FIGS. 1 to 3, however, the sample No. C2 contains more amount of the metallic particles, the sample No. C3 comprises a porous film with a lower porosity, and the sample No. C4 comprises a porous film with a higher porosity.

A measurement of the heat resistance and adhesion force is described.

Heat resistance is measured by performing a test similar to the test for the heat resistance as described above. The inner resistance is measured after 100 hours has passed from the beginning of the test. If the inner resistance is in a range from 0 to 50 kΩ, the sample is classified as "good" with the mark "○". If the inner resistance is in a range from 50 to 100 kΩ, the sample is classified as "medium" with the mark "Δ". If the inner resistance is in a range of 100 kΩ or higher, the sample is classified as "not good" with the mark "×".

In the measurement of the adhesion force, an adhesive tape is adhered to the surface of each of the samples. Then, the adhesive tape is peeled off from the surface at a pulling speed of 5 mm/sec. If no change is observed on the surface the oxygen sensor element, it is classified as "good" with the mark "○". If the porous film or the like is exfoliated, it is classified as "not good" with the mark "×".

As shown in Table 1, the samples No. 1 to No. 6 are superior in both heat resistance and adhesion force. Comparative samples No. C1 and C3 are superior in the adhesion strength, but are inferior in the heat resistance. Comparative samples No. C2 and No. C4 are superior in the heat resistance, but are inferior in the adhesion force.

Thus, it is understood that the oxygen sensor elements of the embodiment is superior in the heat resistance. Furthermore, the bonding between the reaction electrode and the solid electrode is strongly secured. Therefore, the entire structure of the reaction electrode including the porous film is prevented from being exfoliated. Thus, the oxygen sensor element of the embodiment is superior in the durability.

TABLE 1

| Sample Nos. | Metallic Particles Type | Containing Amount (Weight %) | Porousity (%) | Heat Resistance | Adhesion Force |
|---|---|---|---|---|---|
| Embodiments | | | | | |
| 1 | Pt | 1 | 10 | ○ | ○ |
| 2 | Pt | 10 | 10 | ○ | ○ |
| 3 | Pt | 50 | 10 | ○ | ○ |
| 4 | Pt | 10 | 5 | ○ | ○ |
| 5 | Pt | 10 | 20 | ○ | ○ |
| 6 | Rh | 10 | 10 | ○ | ○ |
| Comparative Examples | | | | | |
| C1 | — | 0 | 10 | × | ○ |
| C2 | Pt | 60 | 10 | ○ | × |
| C3 | Pt | 10 | 3 | Δ | ○ |
| C4 | Pt | 10 | 40 | ○ | × |

Another method for manufacturing the oxygen sensor element is described. In this method, the metallic particles to be incorporated into the porous film are added later.

A solid electrolyte is prepared in the same way as the method describe above.

Ceramic particles consisting of $ZrO_2$ particles, each of which has a diameter of about 1 μm, are prepared. A water-soluble slurry comprising an organic binder is added to the ceramic particles, and the mixture is kneaded to obtain a ceramic material. The ceramic material is applied to the surface of the solid electrolyte to provide a ceramic material layer. Then, the ceramic material layer is sintered together with the solid electrolyte at a temperature in a range from 1,400° to 1,600° C. to obtain a ceramic porous film.

By using platinum chloride as the metallic salt, the porous film is immersed into a solution of the metallic salt.

The ceramic porous film containing the metallic salt is heated at a high temperature not lower than 1,200° C. to decompose the metallic salt and to obtain metallic particles therefrom. Then, the metallic particles are aggregated. Thus, a porous film containing metallic particles and ceramic particles can be obtained. By performing the process similar to those described in the above method, a reaction electrode, a coating layer, and an inner electrode are provided to the solid electrolyte; the oxygen sensor element is thereby obtained.

According to the method for manufacturing the oxygen sensor element, the metallic particles can be selectively placed only into the indented portions of the porous film. The same effects as those described in the above method are also obtained.

Figure 5:
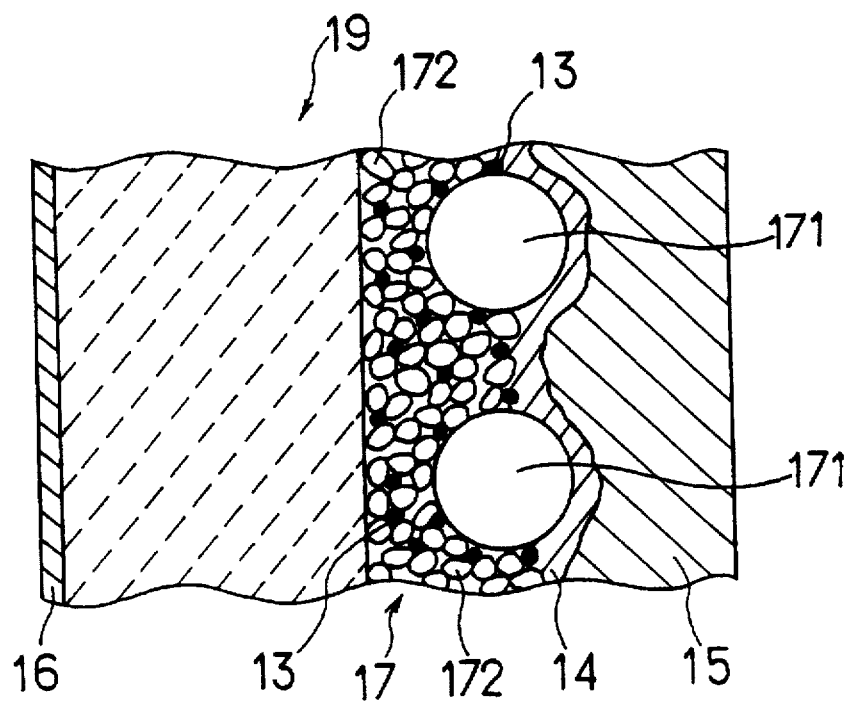
FIG. 5 is a cross sectional view of a main portion of an oxygen sensor element of a second embodiment according to the present invention.

Referring to FIG. 5, a second embodiment according to the present invention is described. In this embodiment, the oxygen sensor element comprises a porous film containing two types of ceramic particles and a metallic particle.

The ceramic particles comprise large granulated particles 171 having a diameter of 50 μm and fine particles 172 having a smaller diameter of 1 μm, both are made of $ZrO_2$. The fine particles function as sintering agents. Platinum particles having a diameter of 1 μm or less are used as the metallic particles 13. The porous film contains the granulated particles 171 in a concentration of 40% by weight, the fine particles 172 in a concentration of 50% by weight, and of the metallic particles 13 in a concentration of 10% by weight.

The diameter of the granulated particles 171 is approximately the same as the thickness of the porous film 17. Thus, numerous protrusions are formed on the surface of the porous film 17 by the granulated particles 171. The other aspects of the oxygen sensor element 19 of this embodiment are the same as the first embodiment.

In the oxygen sensor element 19 of this embodiment, uniform-sized large protrusions are arranged on the surface of the porous film 17, which are formed by large granulated particles 171. Accordingly, the reaction electrode 14 is strongly adhered to the surface of the porous film 17 so as to bite into the large protrusion. The protrusions function effectively as wedges for preventing reaction electrode 14 from being exfoliated. The other effects described for the oxygen sensor element of the first embodiment are also obtained.

While the invention has been described in detail and with reference to specific embodiments thereof, it will be apparent to one skilled in the art that various changes and modifications can be made therein without departing from the spirit and scope thereof.

What is claimed is:

1. An oxygen sensor element for detecting an oxygen concentration, said oxygen sensor comprising:
   a solid electrolyte;
   a porous film provided on said solid electrolyte at a measuring side, said porous film including ceramic particles and metallic particles, said porous film having a porosity in a range of 5–30%; and
   a reaction electrode provided on said porous film, said reaction electrode consisting of a metallic material.

2. An oxygen sensor element according to claim 1, wherein said porous film is baked at a temperature which is not less than a temperature at which aggregation of said metallic particles occurs.

3. An oxygen sensor element according to claim 1, wherein said metallic particles are contained in said porous film in a range from 1 to 50% by weight of said porous film.

4. An oxygen sensor element as claimed in claim 1, wherein an average diameter of said metallic particles is in a range from 0.01 μm–1.0 μm.

* * * * *